United States Patent
Takeshita et al.

(10) Patent No.: US 11,812,140 B2
(45) Date of Patent: Nov. 7, 2023

(54) RECORDING AND REPRODUCTION CONTROL DEVICE, AND RECORDING AND REPRODUCTION CONTROL METHOD

(71) Applicant: JVCKENWOOD Corporation, Yokohama (JP)

(72) Inventors: Hiroshi Takeshita, Yokohama (JP); Yutaka Kuramochi, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 5 days.

(21) Appl. No.: 17/584,447

(22) Filed: Jan. 26, 2022

(65) Prior Publication Data

US 2022/0150396 A1    May 12, 2022

Related U.S. Application Data

(63) Continuation of application No. PCT/JP2020/024920, filed on Jun. 24, 2020.

(30) Foreign Application Priority Data

Aug. 8, 2019    (JP) .................................. 2019-146588

(51) Int. Cl.
*H04N 5/77*    (2006.01)
*H04N 23/66*    (2023.01)
(Continued)

(52) U.S. Cl.
CPC ........... *H04N 23/66* (2023.01); *A61B 5/7292* (2013.01); *G06V 20/41* (2022.01); *H04N 5/265* (2013.01);
(Continued)

(58) Field of Classification Search
None
See application file for complete search history.

(56) References Cited

U.S. PATENT DOCUMENTS

2009/0324131 A1* 12/2009 Tong .......................... G06T 7/75
345/503
2010/0295848 A1* 11/2010 Grewer ..................... G06T 7/11
382/128

(Continued)

FOREIGN PATENT DOCUMENTS

JP    08-322834    12/1996
JP    2001-76078    3/2001
(Continued)

OTHER PUBLICATIONS

International Search Report and Written Opinion for International Application No. PCT/JP2020/024920 dated Sep. 29, 2020, 8 pages.

*Primary Examiner* — Eileen M Adams
(74) *Attorney, Agent, or Firm* — AMIN, TUROCY & WATSON, LLP

(57) ABSTRACT

A recording and reproduction control device includes a moving image data acquisition unit configured to acquire a first video stream from a camera which images a moving image at a predetermined frame rate, a trigger signal acquisition unit configured to acquire a trigger signal from an external device, a captured image generator configured to generate a captured image by one frame from the first video stream at a timing at which the trigger signal is acquired, a storage controller configured to sequentially record the captured images as a second video stream in a storage, a reproduction controller configured to reproduce the second video stream, and a frame interpolation unit configured to interpolate at least one frame image at the predetermined between the captured images and output the captured images and the interpolated frame images which are recorded in array as a third video stream in the storage.

9 Claims, 11 Drawing Sheets

(51) Int. Cl.
*G06V 20/40* (2022.01)
*A61B 5/00* (2006.01)
*H04N 5/265* (2006.01)
*H04N 5/907* (2006.01)
*H04N 5/91* (2006.01)

(52) U.S. Cl.
CPC .............. *H04N 5/77* (2013.01); *H04N 5/907* (2013.01); *H04N 5/91* (2013.01); *G06T 2207/10016* (2013.01); *G06T 2207/30048* (2013.01)

(56) References Cited

U.S. PATENT DOCUMENTS

2017/0186181 A1* 6/2017 Sakas .................... G06T 3/0068
2020/0129740 A1* 4/2020 Kottenstette ........... A61B 34/30

FOREIGN PATENT DOCUMENTS

| JP | 2005-012584 | 1/2005 |
| JP | 2017-131375 | 8/2017 |
| WO | 2009/093693 | 7/2009 |

* cited by examiner ness of this application will be better understood by reading the following detailed description of presently preferred embodiments of the application, when considered in connection with the accompanying drawings.

RECORDING AND REPRODUCTION CONTROL DEVICE, AND RECORDING AND REPRODUCTION CONTROL METHOD

CROSS-REFERENCE TO RELATED APPLICATIONS

This application is a Continuation of PCT International Application No. PCT/JP2020/024920 filed on Jun. 24, 2020 which claims the benefit of priority from Japanese Patent Application No. 2019-146588 filed on Aug. 8, 2019, the entire contents of both of which are incorporated herein by reference.

FIELD

The present disclosure relates to a recording and reproduction control device, a recording and reproduction control method, and a non-transitory storage medium.

BACKGROUND

A technique of detecting, based on an electrocardiogram, a shape of a pulsating heart, for example, a pulsating heart in diastole and generating a pulse signal to sequentially display captured images based on the pulse signal as a trigger, thereby displaying heart images in the same shape, is known (for example, Japanese Laid-open Patent Publication No. H8-322834).

According to Japanese Laid-open Patent Publication No. H8-322834, reproducing the heart image imaged in the past or making high-speed reproduction of a state change of the heart imaged in the past are not taken into consideration.

SUMMARY

A recording and reproduction control device, a recording and reproduction control method, and a non-transitory storage medium are disclosed.

According to one aspect, there is provided a recording reproduction control device comprising: a moving image data acquisition unit configured to acquire moving image data of a predetermined frame rate output from a camera as an input, and to output the moving image as a first video stream; a trigger signal acquisition unit configured to output acquire a trigger signal based on a signal input from an external device; a captured image generator configured to output a captured image by extracting one frame from the first video stream based on the trigger signal is; a frame interpolation unit configured to, with the captured image output from the captured image generator as an input, interpolate at least one frame image at the predetermined frame rate and output the captured image and the interpolated frame image over a period until a new captured image is input; a storage controller configured to sequentially record the captured images output from the captured image generator as a second video stream in a storage and record the captured images and the interpolated frame images in array as a third video stream; and a reproduction controller configured to reproduce the second video stream or the third video stream recorded in the storage, wherein the captured image generator is further configured to input a first captured image and a second captured image chronologically to the frame interpolation unit, and the frame interpolation unit is further configured to interpolate, as the frame image, a mixture image obtained by mixing the first captured image and the second captured image based on a time ratio of a time at which the first captured image was input and a time at which the second captured image was input.

According to one aspect, there is provided a recording and reproduction control method comprising: outputting a first video stream by acquiring moving image data of a predetermined frame rate from a camera; outputting a trigger signal based on a signal input from an external device; outputting a first captured image and a second captured image chronologically by extracting one frame from the first video stream based on the trigger signal; with the first captured image and the second captured image as an input, interpolating at least one frame image at the predetermined frame rate and outputting the captured images and the interpolated frame images over a period until a new captured image is input; sequentially recording the output captured images as a second video stream in a storage and recording the captured images and the interpolated frame images in array as a third video stream; and reproducing the second video stream recorded in the storage, wherein the frame image is a mixture image obtained by mixing the first captured image and the second captured image based on a time ratio of a time at which the first captured image was input and a time at which the second captured image was input.

According to one aspect, there is provided a recording reproduction control device comprising: a moving image data acquisition unit configured to acquire moving image data of a predetermined frame rate output from a camera as an input, and to output the moving image as a first video stream; a trigger signal acquisition unit configured to output a trigger signal based on a signal input from an external device; a captured image generator configured to output a captured image by extracting one frame from the first video stream based on the trigger signal output from the trigger signal acquisition unit; a frame interpolation unit configured to, with the captured image output from the captured image generator as an input, interpolate at least one frame image at the predetermined frame rate and output the captured image and the interpolated frame image over a period until a new captured image is input; a storage controller configured to sequentially record the captured images output from the captured image generator as a second video stream in a storage and record the captured images and the interpolated frame images in array as a third video stream; a reproduction controller configured to reproduce the second video stream or the third video stream recorded in the storage; a timing signal acquisition unit configured to output multiple timing signals based on signals input from multiple types of external devices; a labelling unit configured to assign explanation labels to the first video stream according to the timing signals; and a live moving image storage controller configured to record, in the storage, the first video stream to which the explanation labels output from the labelling unit are assigned.

The above and other objects, features, advantages and technical and industrial significance of this application will be better understood by reading the following detailed description of presently preferred embodiments of the application, when considered in connection with the accompanying drawings.

DETAILED DESCRIPTION OF THE PREFERRED EMBODIMENTS

Figure 1:
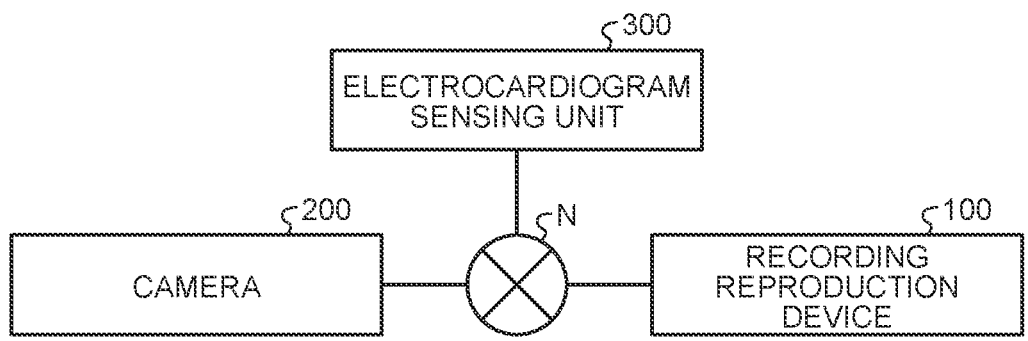
FIG. 1 is a diagram illustrating a configuration of a recording and reproduction system according to each of embodiments of the disclosure.

With reference to the accompanying drawings, details of embodiments according to the disclosure will be described below. The embodiments do not limit the disclosure and, when there are multiple embodiments, embodiments obtained by combining embodiments are covered. In the following embodiments, the same components are denoted by the same reference numerals and thus redundant description will be omitted.

Recording and Reproduction System

A configuration of a recording and reproduction system according to each of embodiments of the disclosure will be described. FIG. 1 is a diagram illustrating an example of a configuration of a recording and reproduction system according to each of the embodiments of the disclosure.

As illustrated in FIG. 1, the recording and reproduction system 1 includes a recording and reproduction device 100, a camera 200, and an electrocardiogram sensing unit 300. The recording and reproduction device 100, the camera 200, and the electrocardiogram sensing unit 300 are connected such that they can communicate with each other via a wireless or wired network N.

The recording and reproduction system 1 according to the embodiment is a system that records images of an internal organ during an operation and reproduces the images. In this case, the camera 200 is, for example, arranged on a ceiling of an operation room. The camera 200 images an affected area on which an operation is being performed and hands of a doctor, or the like, who performs treatment. The camera 200, for example, images changes in a shape or color of the internal organ due to a pulsation of the heart. The electrocardiogram sensing unit 300, for example, monitors a period of the pulsation of the heart of a patient during an operation. Based on the period of the pulsation monitored by the electrocardiogram sensing unit 300, the recording and reproduction device 100 selectively records a video imaged by the camera 200.

In general, a videography recording system that images a manner of operation is arranged in an operation room. The purpose is to record a course of the operation as treatment data and collect academic materials for future.

For example, in a case of a heart operation, the shape of an internal organ varies periodically due to the pulsation of the heart. Due to changes in the blood pressure by the pulsation, the internal organ repeats congestion and ischemia periodically. Accordingly, when this state is imaged sequentially, images in which characters, such as the shape and the color, of the internal organ change periodically are recorded. On the other hand, the characters of the internal organ change also in association with changes in a patient vital sign (hereinafter, also called the vital sign) associated with a progress of the operation. For example, when a decrease in the blood pressure due to a medication or an incision occurs, the internal organ enters an ischemic state.

One of purposes of videography in the operative field is accurately understanding the state change of the internal organ for a long time that occur in association with the change in the patient vital sign associated with the progress of the operation. The state change of the internal organ due to the pulsation however occur constantly and therefore it is difficult to appropriately recognize only the state change of the internal organ that occurs in association with the change in the patient vital sign associated with the progress of the operation. This understanding depends on experiences and skills of the doctor in many cases, which has been a problem.

The recording and reproduction device 100 makes it possible to appropriately recognize only the state change of the internal organ. Specifically, the recording and reproduction device 100 selectively records only frames at times of the same phase of the pulsation (also referred to as key frames below). For example, the recording and reproduction device 100 records only selected key frames sequentially from a key frame time selected at a pulsation phase to a key frame time selected at the next pulsation phase. This makes it possible to save a time of a real period of the pulsation and obtain an operative video moving image content in which only images at the same phase of the pulsation are sequentially recorded.

First Embodiment

Figure 2:
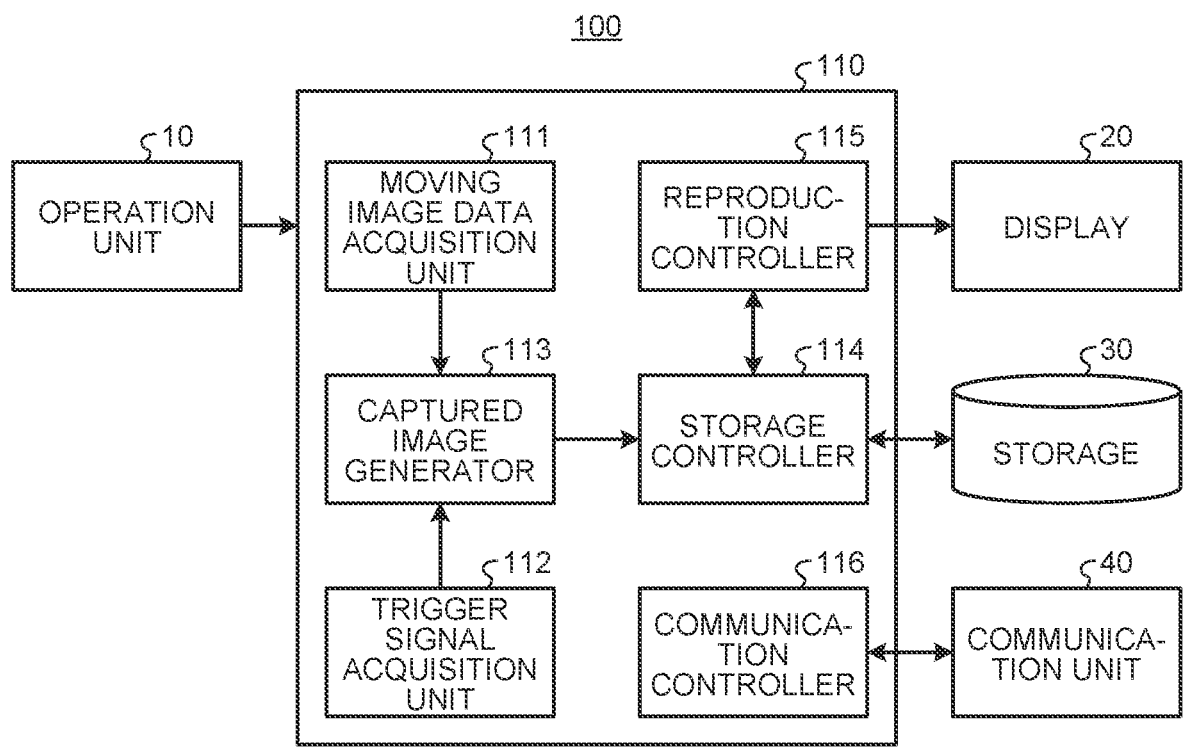
FIG. 2 is a block diagram illustrating an example of a configuration of a recording and reproduction device according to a first embodiment of the disclosure.

Using FIG. 2, a configuration of a recording and reproduction device according to a first embodiment of the disclosure will be described. FIG. 2 is a block diagram illustrating an example of a configuration of a recording and reproduction control device according to the first embodiment of the disclosure.

As illustrated in FIG. 2, the recording and reproduction device 100 includes an operation unit 10, a display 20, a storage 30, a communication unit 40, and a controller (the recording and reproduction control device) 110.

The operation unit 10 receives various operations from a user for the controller 110. The operation unit 10, for example, receives operations for executing various types of processing for the controller 110. The operation unit 10 is, for example, realized by a keyboard, a mouse, and a touch panel.

The display 20 displays various types of information. The display 20, for example, displays various video streams. The display 20, for example, displays a video stream acquired by a moving image data acquisition unit 111 or a video stream generated by a captured image generator 113. The display 20 is, for example, a display including a liquid crystal display (LDC) or an organic electro-luminescence (EL) display. When the operation unit 10 consists of a touch panel, the display 20 is formed integrally with the operation unit 10.

The storage 30 records various types of information. The storage 30, for example, records various video streams. The storage 30, for example, records various video streams generated by the controller 110. The storage 30 is, for example, implemented by a semiconductor memory device, such as a random access memory (RAM) or a flash memory, or a storage device, such as a hard disk or an optical disk.

The communication unit 40 is, for example, implemented by a network interface card (NIC), a communication circuit, or the like. The communication unit 40 has a wired or wireless connection to the network N (such as the Internet). The communication unit 40 transmits and receives information to and from other devices, etc., via the network N. The communication unit 40, for example, transmits and receives information to and from the camera 200 and the electrocardiogram sensing unit 300.

The controller 110 is, for example, implemented by a central processing unit (CPU) or a micro processing unit (MPU) by executing a program recorded in a storage (not illustrated in the drawing) using a random access memory (RAM), or the like, as a work area. The controller 110 is a controller that may be implemented by an integrated circuit, such as an application specific integrated circuit (ASIC) or a field programmable gate array (FPGA). The controller 110 includes the moving image data acquisition unit 111, a trigger signal acquisition unit 112, the captured image generator 113, a storage controller 114, a reproduction controller 115, and a communication controller 116.

The moving image data acquisition unit 111 acquires various types of moving image data. The moving image data acquisition unit 111 acquires various video streams. The moving image data acquisition unit 111 acquires the video stream from the camera 200 via the communication unit 40. The video stream acquired by the moving image data acquisition unit 111 from the camera 200 is also referred to as a first video stream. The moving image data acquisition unit 111 outputs the acquired first video stream to the captured image generator 113.

The trigger signal acquisition unit 112 acquires a trigger signal from an external device. The trigger signal acquisition unit 112, for example, acquires a trigger signal from the electrocardiogram sensing unit 300. The trigger signal acquisition unit 112 outputs the acquired trigger signal to the captured image generator 113.

Figure 3:
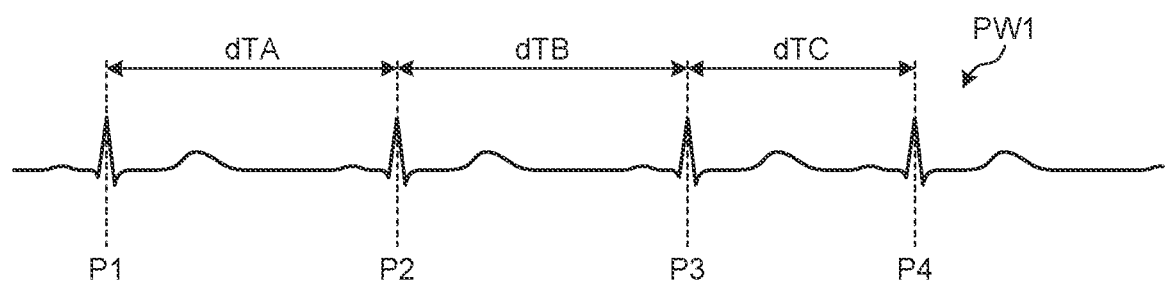
FIG. 3 is a diagram for explaining an example of a trigger signal according to each of the embodiments of the disclosure.

Using FIG. 3, the trigger signal according to the embodiments of the disclosure will be described. FIG. 3 is a diagram for explaining an example of the trigger signal according to each of the embodiments of the disclosure.

FIG. 3 illustrates an electrocardiogram waveform PW1 of a patient during an operation. The electrocardiogram waveform PW1 is an electrocardiogram of a patient during an operation that is measured by the electrocardiogram sensing unit 300. The electrocardiogram sensing unit 300 outputs a pulse signal at a timing synchronized with a specific phase in the electrocardiogram waveform PW1. The electrocardiogram sensing unit 300 outputs pulse signals at a phase P1, a phase P2, a phase P3 and a phase P4 indicating peak values in the electrocardiogram waveform PW1. In this case, the trigger signal acquisition unit 112 acquires the pulse signals that are output from the electrocardiogram sensing unit 300 as trigger signals. An interval dTA between the phase P1 and the phase P2, an interval dTB between the phase P2 and the phase P3, and an interval dTC between the phase P3 and the phase P4 may be equal to one another or may be different from one another.

In the first embodiment, the trigger signal described using FIG. 3 is an example and does not limit the disclosure. The trigger signal may be some other vital sign information. For example, the trigger signals may be signals that are output at the same specific phase in a result of measuring breaths and blood pressures obtained by measuring a breath and a blood pressure constantly. The trigger signals may be signals that are output when it is determined that the internal organ has the same specific shape by executing an image recognition processing on imaged images of the internal organ of the patient.

FIG. 2 will be referred to again. The captured image generator 113 generates a captured image. The captured image generator 113 generates a captured image from the first video stream acquired by the moving image data acquisition unit 111. The captured image generator 113, for example, generates a captured image by one frame from the first video stream at the timing at which the trigger signal acquisition unit 112 acquires the trigger signal. The captured image generator 113 outputs the generated captured image to the storage controller 114.

The storage controller 114 records various types of information in the storage 30. The storage controller 114, for example, generates a second video stream by arranging captured images generated by the captured image generator 113 in time series. The storage controller 114 records the generated second video stream in the storage 30.

Figure 4:
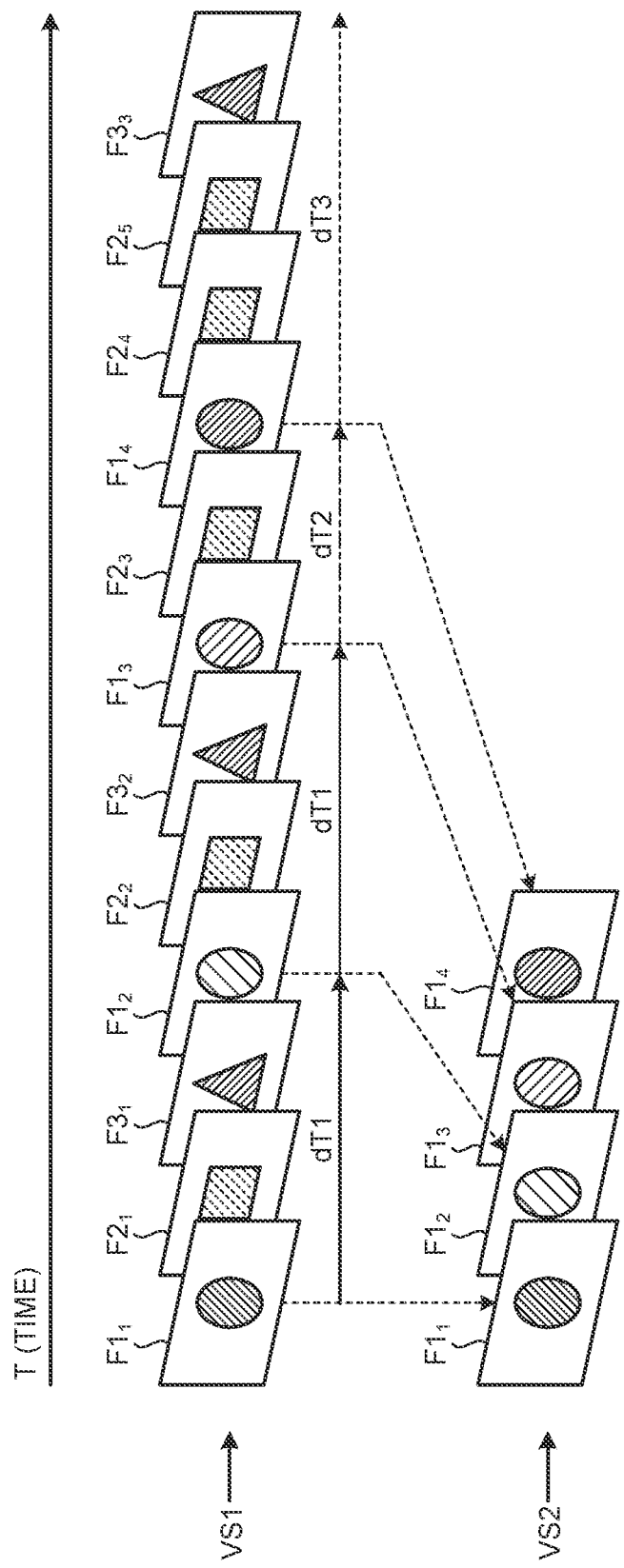
FIG. 4 is a diagram for explaining an example of a method of generating a second video stream from a first video stream.

Using FIG. 4, an example of a method of generating a second video stream from a first video stream will be described. FIG. 4 is a diagram for explaining an example of the method of generating a second video stream from a first video stream.

As illustrated in FIG. 4, a first video stream VS1 consists of multiple frame images. The first video stream VS1 includes a frame image $F1_1$, a frame image $F1_2$, a frame image $F1_3$, and a frame image $F1_4$. The first video stream VS1 includes a frame image $F2_1$, a frame image $F2_2$, a frame image $F2_3$, a frame image $F2_4$, and a frame image $F2_5$. The first video stream VS1 includes a frame image $F3_1$, a frame image $F3_2$, and a frame image $F3_3$. The frame images $F1_1$ to $F1_4$ are represented by "○". The frame images $F2_1$ to $F2_5$ are represented by "□". The frame images $F3_1$ to $F3_3$ are represented by "△". "○", "□" and "△" schematically represent the state of the pulsation of the internal organ (for example, the heart). In other words, the frame images $F1_1$ to $F1_4$ represent the same state of the pulsation of the internal organ. The frame images $F2_1$ to $F2_5$ represent the same state of the pulsation of the internal organ. The frame images $F3_1$ to $F3_3$ represent the same state of the pulsation of the internal organ. In other words, the frame images $F1_1$ to $F1_4$ are frame images that are imaged at the same phase of a pulse waveform. The frame images $F2_1$ to $F2_5$ are frame images that are imaged at the same phase of the pulse waveform. The frame images $F3_1$ to $F3_5$ are frame images that are imaged at the same phase of the pulse waveform. The differences in hatching mean differences in color of the internal organ due to congestion and ischemia. In other words, combinations of the shapes and the colors of the internal organ are represented and, particularly, according to the disclosure, changes in color with the same shape of the internal organ in a second video stream VS2 described below are observed.

The captured image generator 113 generates a captured image by one frame from the first video stream VS1 at the timing when the trigger signal acquisition unit 112 acquires a trigger signal. In other words, the captured image generator 113 generates, as captured images, frame images that are imaged at the same phase of the pulse waveform among the frame images contained in the first video stream VS1. The captured image generator 113 generates, as key frame images, the frame image $F1_1$, the frame image $F1_2$, the frame image $F1_3$ and the frame image $F1_4$ as the captured images. The time interval between the frame image $F1_1$ and the frame image $F1_2$ is dT1. The time interval between the frame image $F1_2$ and the frame image $F1_3$ is dT1. The time interval between the frame image $F1_3$ and the frame image $F1_4$ is dT2. The time interval between the frame image $F1_4$ and the frame image at the next same phase is dT3. As described above, the time intervals between frame images at the same phase may differ.

The storage controller 114 generates the second video stream VS2 by arranging the frame image $F1_1$, the frame image $F1_2$, the frame image $F1_3$, and the frame image $F1_2$ in time series. The storage controller 114 records the generated second video stream VS2 in the storage 30.

The reproduction controller 115 reproduces various video streams and displays the video streams on the display 20. The reproduction controller 115, for example, reproduces the second video stream recorded in the storage 30 and displays the second video stream on the display 20.

The communication controller 116 controls various type of communication via the communication unit 40. The communication controller 116 controls communications between the camera 200 and the electrocardiogram sensing unit 300.

Figure 5:
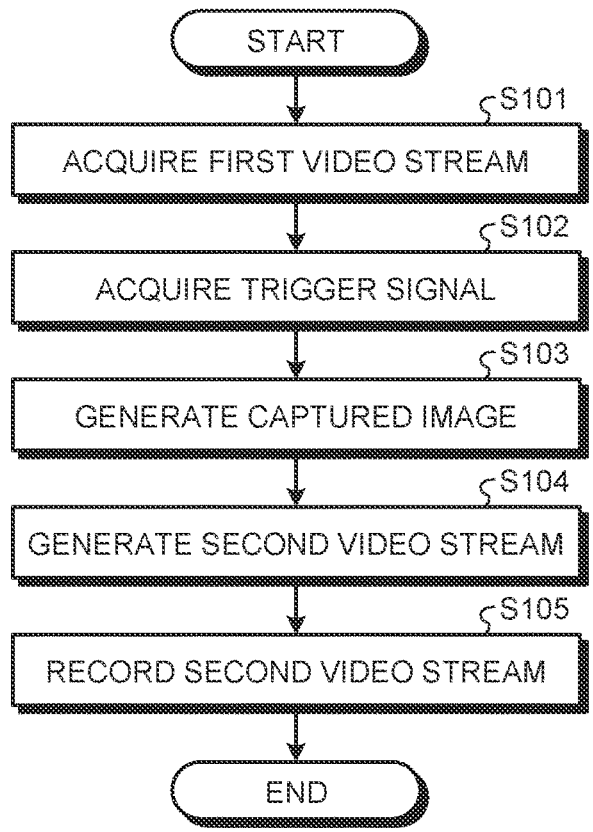
FIG. 5 is a flowchart illustrating an example of a flow of processes performed by a controller of the recording and reproduction device according to the first embodiment of the disclosure.

Using FIG. 5, a flow of processes of storing the second video stream that is performed by the controller 110 according to the first embodiment will be described. FIG. 5 is a flowchart illustrating an example of the flow of the processes of storing the second video stream that is performed by the controller 110 according to the first embodiment of the disclosure.

The controller 110 acquires a first video stream (step S101). Specifically, the moving image data acquisition unit 111 acquires a first video stream from the camera 200. The controller 110 then proceeds to step S102.

The controller 110 acquires a trigger signal (step S102). Specifically, the trigger signal acquisition unit 112 acquires a trigger signal from the electrocardiogram sensing unit 300. The controller 110 then proceeds to step S103.

The controller 110 generates a captured image (step S103). Specifically, based on the trigger signal acquired by the trigger signal acquisition unit 112, the captured image generator 113 generates a captured image from the first video stream acquired by the moving image data acquisition unit 111. The controller 110 then proceeds to step S104.

The controller 110 generates a second video stream (step S104). Specifically, the storage controller 114 generates a second video stream by arranging the captured images generated by the captured image generator 113 in time series. The controller 110 then proceeds to step S105.

The controller 110 records the second video stream (step S105). Specifically, the storage controller 114 records the second video stream t generated at step S104 in the storage 30. The processes in FIG. 5 then end.

Figure 6:
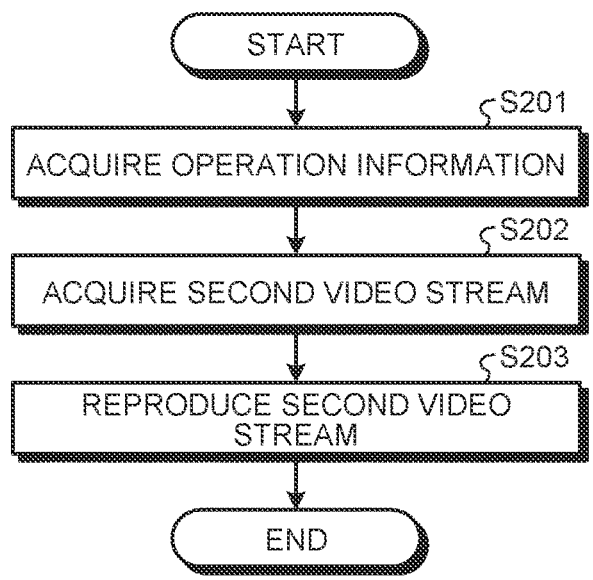
FIG. 6 is a flowchart illustrating an example of a flow of processes performed by the controller of the recording and reproduction device according to the first embodiment of the disclosure.

Using FIG. 6, a process of reproducing the second video stream recorded in the storage 30 will be described. FIG. 6 is a flowchart illustrating an example of the processes of reproducing the second video stream recorded in the storage 30.

First of all, the controller 110 acquires operation information (step S201). Specifically, the storage controller 114 acquires operation information indicating that the second stream is to be reproduced from the operation unit 10. The controller 110 then proceeds to step S202.

The controller 110 acquires the second video stream (step S202). Specifically, the storage controller 114 acquires the second video stream from the storage 30. The controller 110 then proceeds to step S203.

The controller 110 reproduces the second video stream (step S203). Specifically, the reproduction controller 115 reproduces the second video stream acquired by the storage controller 114. The processes in FIG. 6 then end.

As described above, according to the first embodiment, it is possible to record the second video stream generated based on the first video stream and reproduce the recorded second video stream. This makes it possible to obtain an operative video moving image content in which only images at the same phase of the pulsation are sequentially recorded. The second video stream consists of only the key frames corresponding to the same phase of the pulsation and characters of the internal organ, such as the shape or the color, approximately coincide. This enables the user to easily recognize the state change of the internal organ by only checking the second video stream by sight.

In the first embodiment, generating the second video stream makes it possible to observe only the state change of the internal organ for a long time due to the change in the patient vital sign associated with the progress of the operation along time axis.

Second Embodiment

Figure 7:
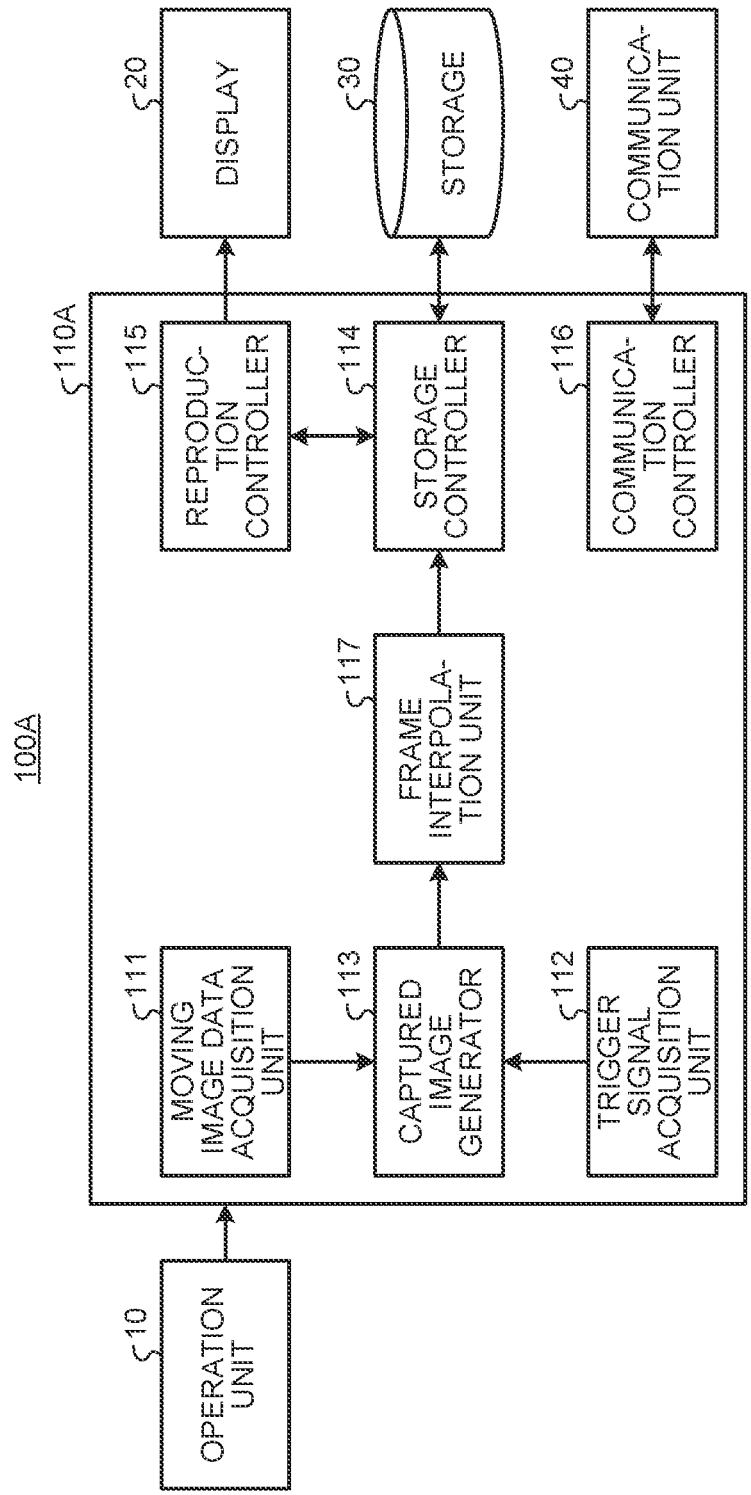
FIG. 7 is a block diagram illustrating an example of a configuration of a recording and reproduction device according to a second embodiment of the disclosure.

Using FIG. 7, a recording and reproduction device according to a second embodiment of the disclosure will be described. FIG. 7 is a block diagram illustrating an example of a configuration of the recording and reproduction device according to the second embodiment of the disclosure.

As illustrated in FIG. 7, a recording and reproduction device 100A is different from the recording and reproduction device 100 illustrated in FIG. 2 in that a controller 110A includes a frame interpolation unit 117.

The frame interpolation unit 117 interpolates at least one frame image between various captured images. The frame interpolation unit 117, for example, receives a captured image from the captured image generator 113. The frame interpolation unit 117, for example, interpolates at least one frame image at a predetermined frame rate until the received captured image is updated, that is, until the next captured image is received and outputs the images to the storage controller 114. In this case, the storage controller 114 records the captured images and the frame images in array as a third video stream in the storage 30.

The frame interpolation unit 117, for example, inputs a captured image that is input from the captured image generator 113 previously as a frame image. Specifically, for example, when a first captured image is input from the captured image generator 113, the frame interpolation unit 117 interpolates the first captured image as a frame image until the next captured image that is a second captured image is input. When the second captured image is input, the frame interpolation unit 117 interpolates the second captured image as a frame image until the next captured image that is a third captured image is input.

The frame interpolation unit 117 may generate a mixture image by mixing the first captured image and the second first captured image based on a time ratio of the time at which the first captured image was generated and the time at which the second captured image was generated to interpolate the mixture image. Specifically, the frame interpolation unit 117 may generate a mixture image indicating the state of the internal organ at a time between the time of the first captured image and the time of the second captured image. In this case, the storage controller 114 records the captured images and the mixture images in array as the third video stream in the storage 30.

Figure 8:
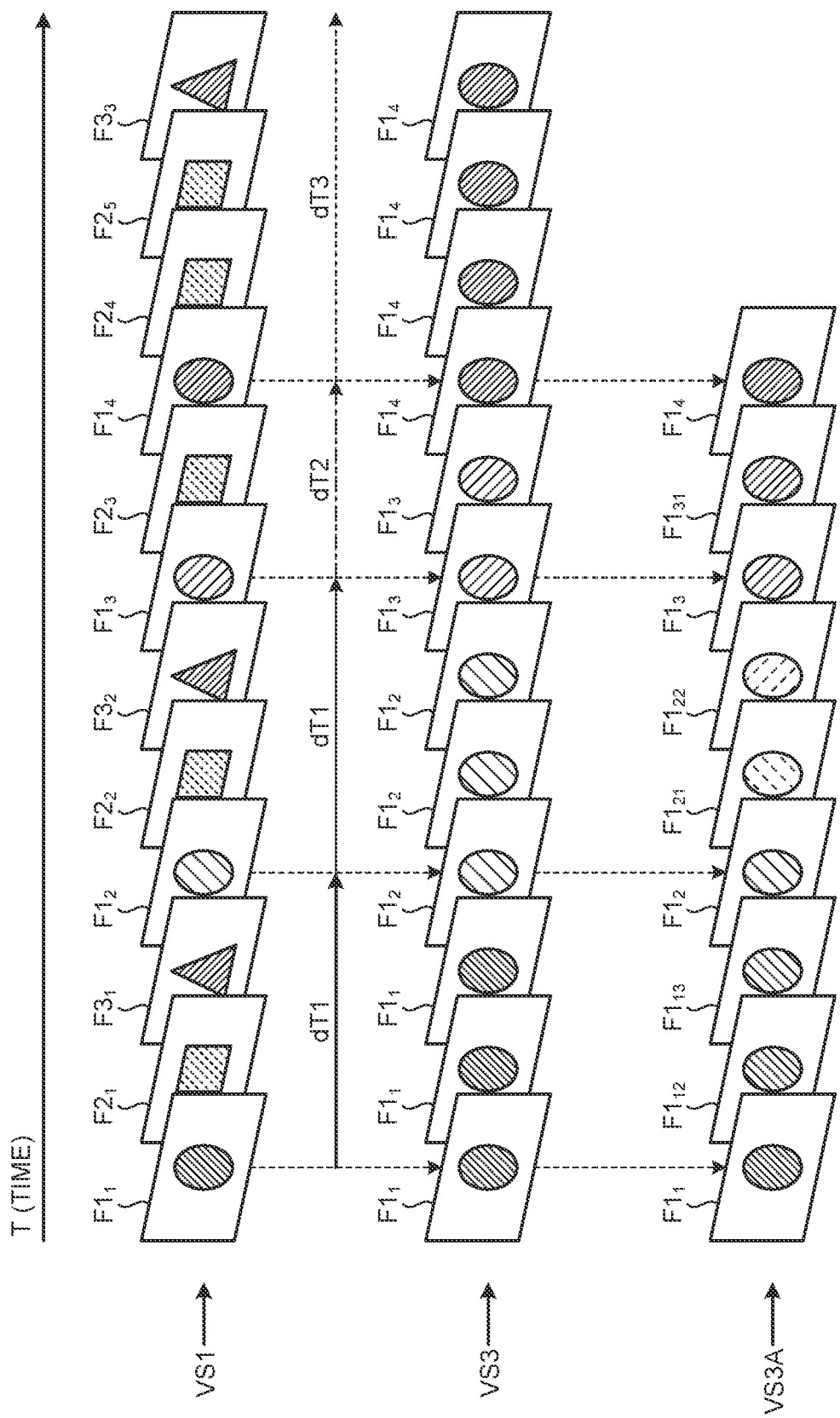
FIG. 8 is a diagram for explaining an example of a method of generating a third video stream from the first video stream.

Using FIG. 8, a method of generating a third video stream from a first video stream will be described. FIG. 8 is a diagram for explaining an example of the method of generating a third video stream from a first video stream.

Using FIG. 8, a case in which the captured image generator 113 generates a frame image $F1_1$, a frame image $F1_2$, a frame image $F1_3$, and a frame image $F1_4$ as key frame images is considered.

When the frame image $F1_1$ is input, the frame interpolation unit 117 interpolates the frame image $F1_1$ at a predetermined frame rate until the frame image $F1_2$ is input. When the frame image $F1_2$ is input, the frame interpolation unit 117 interpolates the frame image $F1_2$ at a predetermined frame rate until the frame image $F1_3$ is input. When the frame image $F1_3$ is input, the frame interpolation unit 117 interpolates the frame image $F1_3$ at a predetermined frame rate until the frame image $F1_4$ is input. When the frame image $F1_4$ is input, the frame interpolation unit 117 interpolates the frame image $F1_4$ at a predetermined frame rate until the next frame image is input. The storage controller 114 aligns the images in time series and records the images as a third video stream VS3 in the storage 30.

The frame interpolation unit 117, for example, may interpolate the mixture images between the frame image F1/ and the frame image $F1_2$. As illustrated in FIG. 8, the frame interpolation unit 117, for example, may interpolate a mixture image $F1_{12}$ and a mixture image $F1_{13}$ between the frame image $F1_1$ and the frame image $F1_2$. The state of the mixture image $F1_{12}$ is closer to the state of the frame $F1_1$ than that of the frame $F1_2$. The state of the mixture image $F1_{13}$ is closer to the state of the frame $F1_2$ than that the frame $F1_1$. Similarly, the frame interpolation unit 117 interpolates a mixture image $F1_{21}$ and a mixture image $F1_{22}$ between the frame image $F1_2$ and the frame image $F1_3$. Similarly, the frame interpolation unit 117 interpolates a mixture image $F1_{31}$ between the frame image $F1_3$ and the frame image $F1_4$. The storage controller 114 aligns the images in time series and records the images as a third video stream VS3A in the storage 30. By checking the third video stream VS3A by sight makes it possible to check how the state changes gradually.

Figure 9:
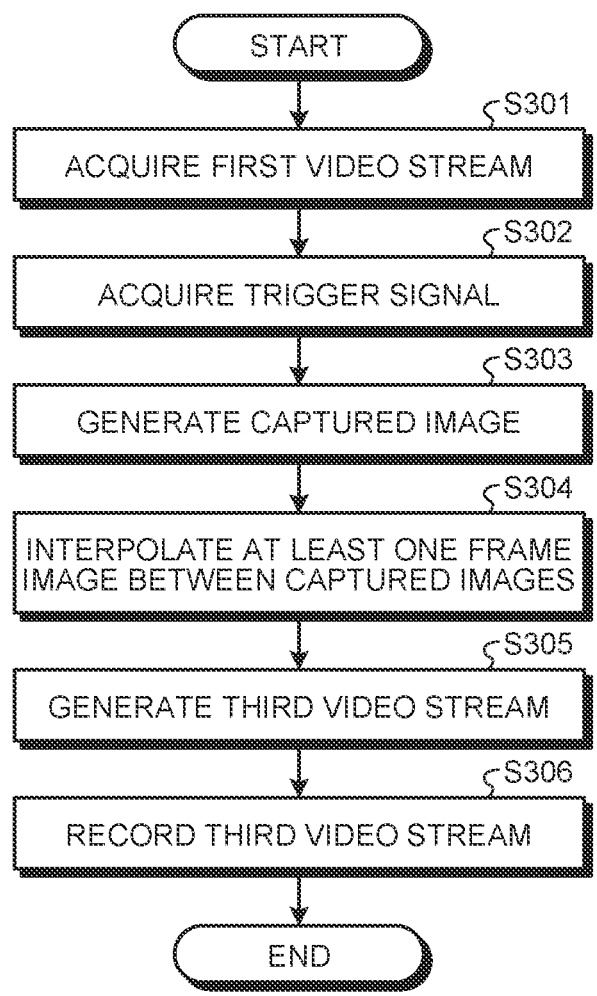
FIG. 9 is a flowchart illustrating an example of a flow of processes performed by a controller of the recording and reproduction device according to the second embodiment of the disclosure.

Using FIG. 9, a flow of processes of storing a third video stream that is performed by the controller 110A according to the second embodiment of the disclosure will be described. FIG. 9 is a flowchart illustrating an example of a flow of processes of storing a third video stream that is performed by the controller 110 according to the second embodiment of the disclosure.

The sets of processing of steps S301 to step S303 are the same as those of steps S101 to S103, respectively, and thus description thereof will be omitted.

The controller 110A interpolates at least one frame image between captured images (step S304). Specifically, the frame interpolation unit 117 interpolates at least one frame image at a predetermined frame rate between the captured images. The controller 110A then goes to step S305.

The controller 110A generates a third video stream (step S305). Specifically, the storage controller 114 generates a video stream by arranging the captured images and the interpolated frames in time series. The controller 110A then proceeds to step S306.

The controller 110A records the third video stream (step S306). Specifically, the storage controller 114 records the third video stream generated at step S305 in the storage 30. The processes in FIG. 9 then end.

The process of reproducing the third video stream employs the same method as the method of reproducing the second video stream illustrated in FIG. 6 and thus description thereof will be omitted. In the second embodiment, the reproduction controller 115 may reproduce the third video stream at a high speed by reproducing, at a predetermined frame rate, frame images that are sampled at a predetermined period from a third stream. The period at which sampling is performed on the third video stream is not particularly limited. For example, the user can set any period at which sampling is performed on the third video stream by an operation by the operation unit 10.

Figure 10:
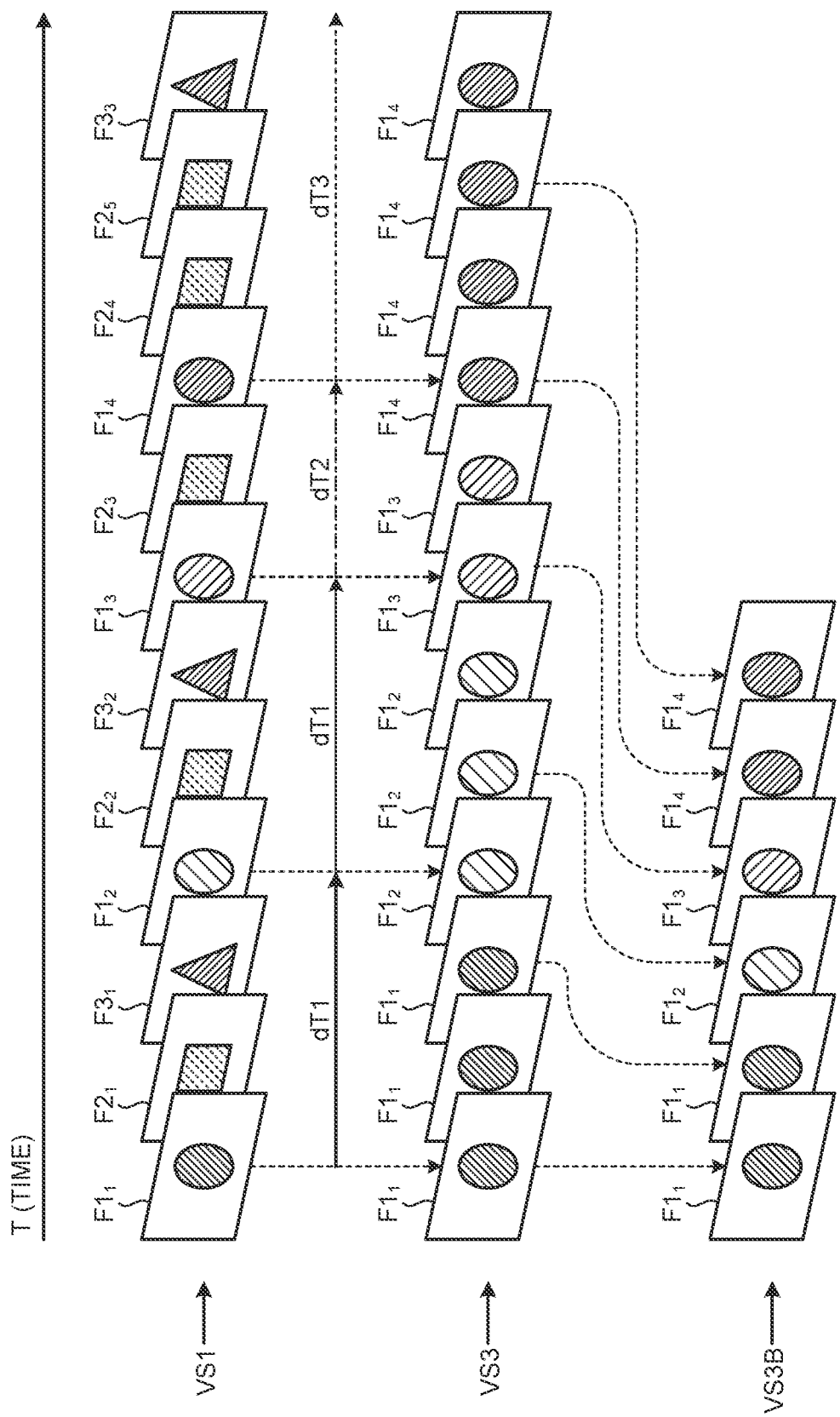
FIG. 10 is a diagram for explaining an example of a method of a high-speed reproduction of the third video stream.

Using FIG. 10, an example of a method of reproducing the third video stream at a high speed will be described. FIG. 10 is a diagram for explaining the example of the method of reproducing a third video stream at a high speed.

As illustrated in FIG. 10, the reproduction controller 115 may, for example, sample 12 frame images contained in the third video stream VS3 at every two frame images and reproduce the frame images as a third video stream VS3B. In this case, the third video stream VS3B includes six frames that are the frame image $F1_1$, the frame image $F1_1$, the frame image $F1_2$, the frame image $F1_3$, the frame image $F1_4$, and the frame image $F1_4$. Sampling the frame images as described above enables the reproduction controller 115 to reproduce the third video stream VS3 at a high speed.

Figure 11:
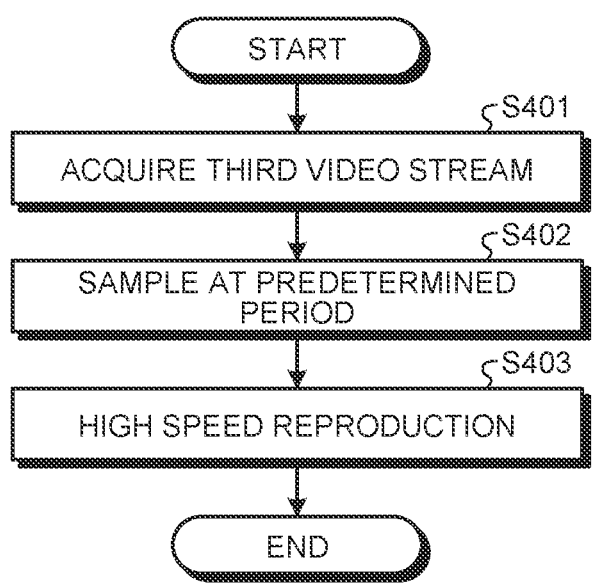
FIG. 11 is a flowchart illustrating an example of a flow of processes of a high-speed reproduction of the third video stream performed by the controller of the recording and reproduction device according to the second embodiment of the disclosure.

Using FIG. 11, an example of a flow of processes of reproducing the third video stream at a high speed that is performed by the controller 110A according to the second embodiment of the disclosure will be described. FIG. 11 is a flowchart illustrating the example of the flow of the processes of reproducing the third video stream at a high speed that is performed by the controller 110A according to the second embodiment of the disclosure.

First of all, the controller 110A acquires a third video stream (step S401). Specifically, the storage controller 114 acquires a third video stream from the storage 30. The controller 110A then proceeds to step S402.

The controller 110A samples the third video stream at a predetermined period (step S402). Specifically, a reproduction controller 125 samples the third video stream at a predetermined period. The controller 110A then proceeds to step S403.

The controller 110A reproduces the third video stream at a high speed (step S403). Specifically, the third video stream sampled by the reproduction controller 125 at step S402 is reproduced at a high speed. The processes in FIG. 11 then end.

As described above, according to the embodiment, interpolating specific frame images between the captured images enables to coincide the time of reproduction of the video stream with a real time. This makes it possible to easily recognize a temporal change in a pulsation period of the internal organ.

In the second embodiment, it is possible to reproduce the recorded video stream at a high speed. Accordingly, it is possible to check the shape or the characters of the internal organ at a high speed.

Third Embodiment

Figure 12:
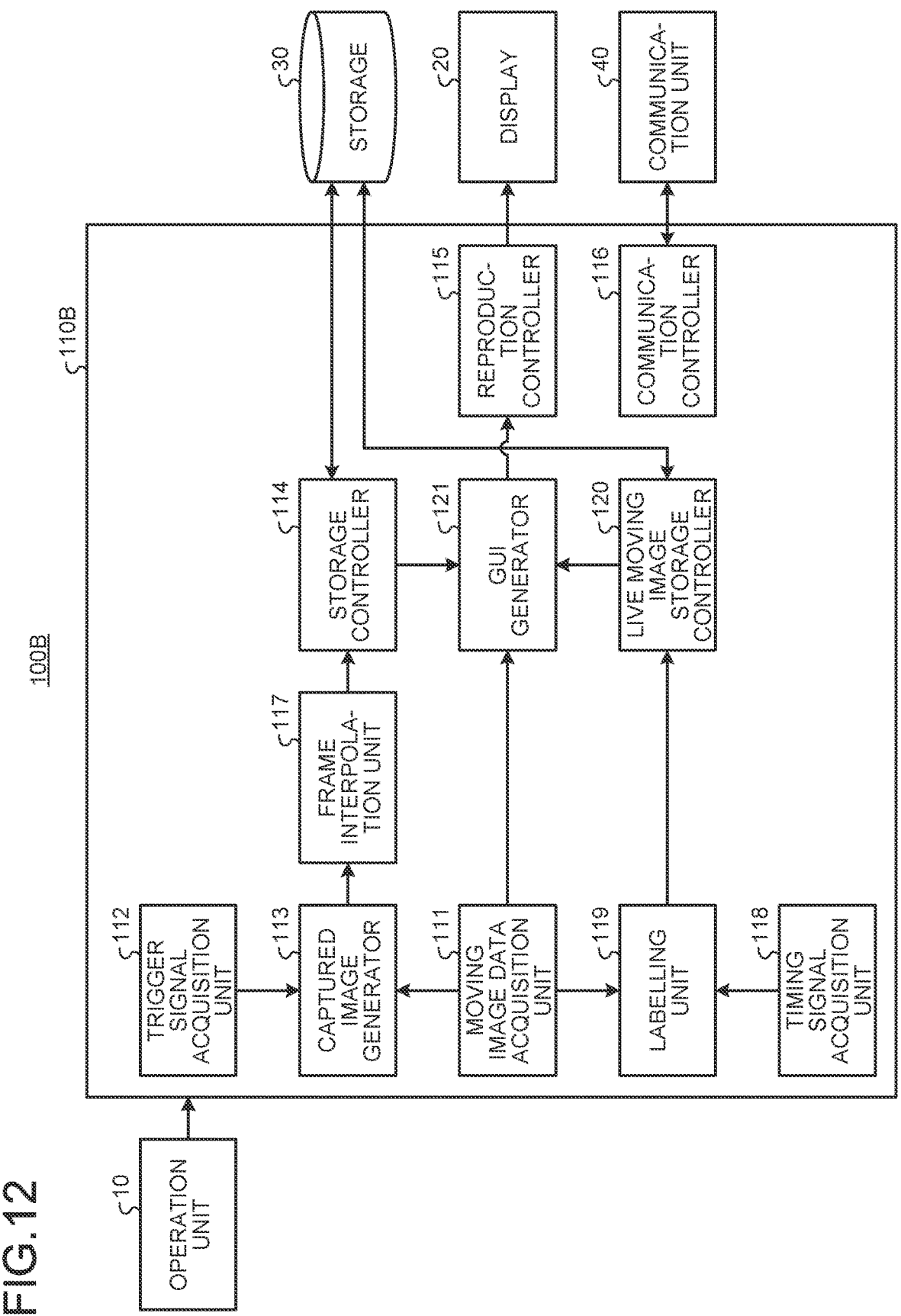
FIG. 12 is a block diagram illustrating an example of a configuration of a recording and reproduction control device according to a third embodiment of the disclosure.

Using FIG. 12, a recording and reproduction device according to a third embodiment of the disclosure will be described. FIG. 12 is a block diagram illustrating an example of a configuration of the recording and reproduction device according to the third embodiment of the disclosure.

As illustrated in FIG. 12, a recording and reproduction device 100B is different from the recording and reproduction device 100 illustrated in FIG. 2 in that a controller 110B includes the frame interpolation unit 117, a timing signal acquisition unit 118, a labelling unit 119, a live moving image storage controller 120, and a GUI generator 121.

The timing signal acquisition unit 118 acquires multiple types of a timing signal from external devices. The timing signal acquisition unit 118 outputs the acquired timing signal to the labelling unit 119. The timing signal, for example, includes information on the time. The timing signal contains, for example, vital sign information on a patient. The timing signal, for example, includes information on each type of treatment applied to the patient.

The labelling unit 119 receives a first video stream from the moving image data acquisition unit 111. The labelling unit 119, for example, assigns an explanation label to the first video stream. The labelling unit 119, for example, assigns a chapter to the first video stream. The labelling unit 119, for example, assigns an explanation label and a chapter to the first video stream according to the timing signal that is received from the timing signal acquisition unit 118. The labelling unit 119, for example, may recognize a content of treatment by executing an image recognition process on the first video stream and assign the recognized treatment as an explanation label. The labelling unit 119, for example, outputs the first video stream to which the explanation label and the chapter are assigned to the live moving image storage controller 120.

The live moving image storage controller 120 records the first video stream to which the explanation label and the chapter are assigned in the storage 30. The live moving image storage controller 120 outputs the first video stream to which the explanation label and the chapter are assigned to the GUI generator 121.

The GUI generator 121 generates a GUI on which various video streams are displayed. The GUI generator 121, for example, generates a GUI containing a window on which the first video stream is displayed. The GUI generator 121 generates thumbnail images based on the frame images contained in the first video stream and generates a GUI containing a timeline display in which thumbnail images with names of events are aligned in time series. The event contains, for example, time information, various types of treatment, and vital sign information on the patient. When a thumbnail image of the timeline display is clicked, the GUI generator 121 generates a GUI containing a window for reproducing the third video stream before and after the time at which the thumbnail image was recorded.

Figure 13:
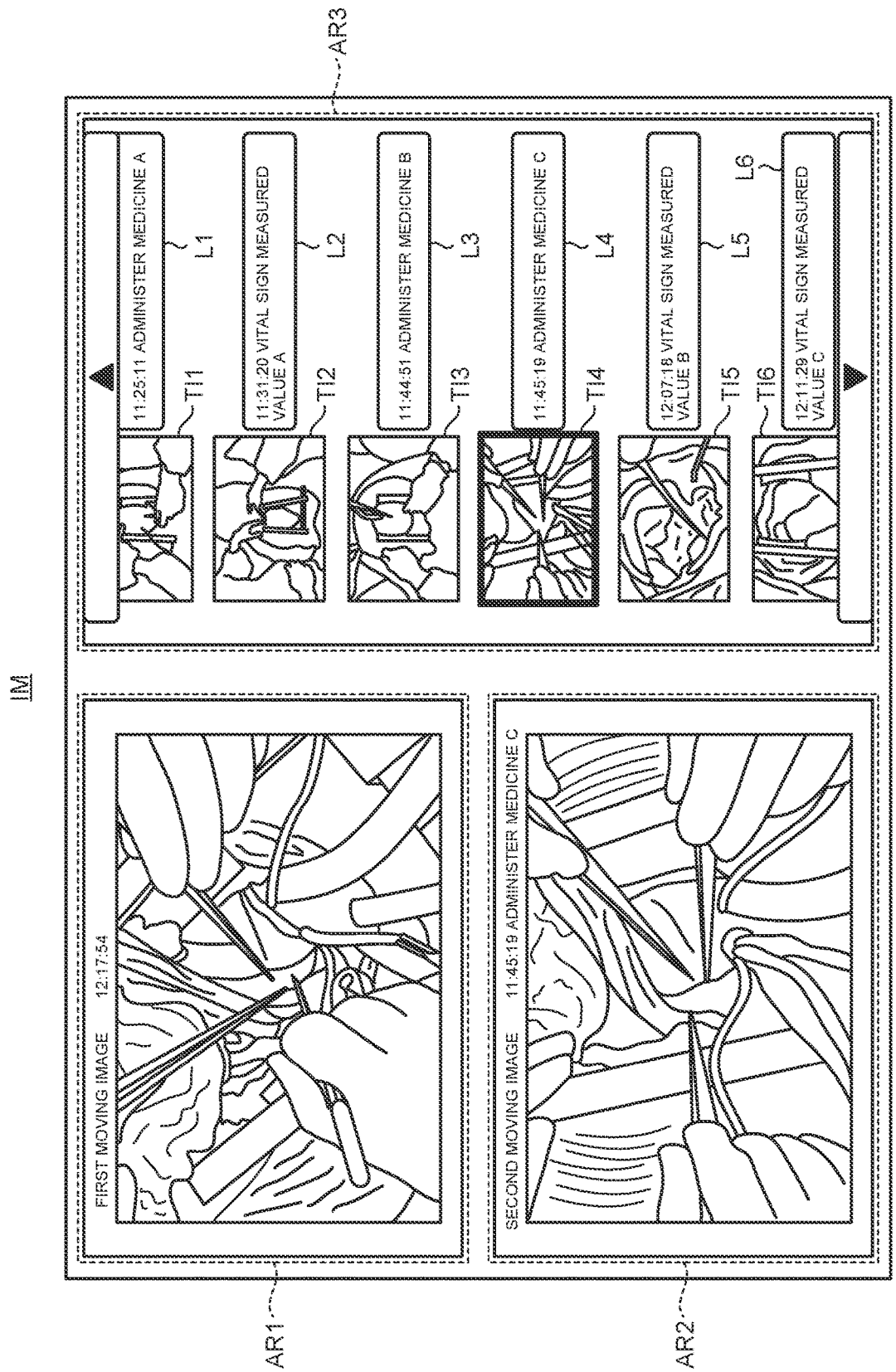
FIG. 13 is a diagram for explaining an example of a GUI (graphical user interface) generated by the recording and reproduction control device according to the third embodiment of the disclosure.

Using FIG. 13, a GUI that is generated by a recording and reproduction control device according to the third embodiment of the disclosure will be described. FIG. 13 is a diagram for explaining an example of the GUI that is generated by the recording and reproduction control device according to the third embodiment of the disclosure.

A display screen IM illustrated in FIG. 13 is an example of a GUI that is generated by the recording and reproduction device 100. The display screen IM includes a first area AR1, a second area AR2, and a third area AR3.

A first moving image is displayed in the first area AR1. The first moving image is, for example, the first video stream. In other words, a live video of an operation is displayed in the first area AR1. Note that a video other than the live video of the operation may be displayed in the first area AR1. For example, a video before the present time 12:17:54 may be displayed in the first area AR1. In this case, a video different from the video displayed in the second area AR2 may be displayed in the first area AR1.

In the second area AR2, a second moving image different form the first moving image is displayed. For example, a video before the present time is displayed in the second area AR2. In the second area AR2, for example, a video before or after the time at which the thumbnail image selected in the third area AR3 was recorded is displayed for a predetermined time. In the example illustrated in FIG. 13, a video before or after a thumbnail TI4 that is selected in the third area AR3 is displayed in the second area AR2. The predetermined time may be set freely by the user. In the example illustrated in FIG. 13, a video of administration of a medicine C at 11:45:19 is displayed.

In the third area AR3, a time line in which the thumbnail images with names of events are aligned in time series is displayed. In the example illustrated in FIG. 13, labels L1 to L6 are associated with thumbnail images TI1 to TI6. The labels L1 to L6 contain information on the events. For example, information indicating that a medicine A is administered at 11:25:11 is associated with the thumbnail image T1. For example, information indicating that the state of the vital sign is a vital sign measured value A at 11:31:20 is associated with the thumbnail image TI2. As described above, various types of treatment and vital sign information on the patient are associated with each of the thumbnail images displayed in the third area AR3.

As described above, in the third embodiment, generating a GUI makes it possible to reproduce the state change of the internal organ for a long time due to the change of the vital sign of the patient associated with the progress of the operation along the time axis to be observed. In the third embodiment, it is possible to easily compare the states of the internal organ at different times.

The embodiments of the disclosure have been described and the content of the embodiments do not limit the disclosure. The recording and reproduction system has the configuration in which the camera 200 and the electrocardiogram sensing unit 300 are connected to the recording and reproduction device 100 via the network. However, the configuration is not limited thereto, and a configuration in which the connection is made by a method other than a network may be employed.

According to the disclosure, it is possible to record images of an internal organ and reproduce the images in various modes.

Although the application has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A recording reproduction control device comprising:
a hardware processor that executes machine-executable units, comprising:
a moving image data acquisition unit configured to acquire moving image data of a predetermined frame rate output from a camera as an input, and to output the moving image as a first video stream;
a trigger signal acquisition unit configured to output a trigger signal based on a signal input from an external device;
a captured image generator unit configured to output a captured image by extracting one frame from the first video stream based on the trigger signal output from the trigger signal acquisition unit;
a frame interpolation unit configured to, with the captured image output from the captured image generator unit as an input, interpolate at least one frame image at the predetermined frame rate and output the captured image and the interpolated frame image over a period until a new captured image is input;
a storage controller unit configured to sequentially record the captured images output from the captured image generator unit as a second video stream in a storage and record the captured images and the interpolated frame images in array as a third video stream; and
a reproduction controller unit configured to reproduce the second video stream or the third video stream recorded in the storage,
wherein the captured image generator unit is further configured to input a first captured image and a second captured image chronologically to the frame interpolation unit, and
the frame interpolation unit is further configured to interpolate, as the frame image, a mixture image obtained by mixing the first captured image and the second captured image based on a time ratio of a time at which the first captured image was input and a time at which the second captured image was input.

2. The recording and reproduction control device according to claim 1, wherein the trigger signal is generated at a timing that is synchronized with a specific phase of an electrocardiogram based on information acquired from the electrocardiogram.

3. The recording and reproduction control device according to claim 1, wherein the reproduction controller unit is further configured to reproduce, at the predetermined frame rate, the frame images that are sampled at a period different from a period of the trigger signal from the third video stream.

4. A recording reproduction control device comprising:
a hardware processor that executes machine-executable units, comprising:
a moving image data acquisition unit configured to acquire moving image data of a predetermined frame rate output from a camera as an input, and to output the moving image as a first video stream;
a trigger signal acquisition unit configured to output a trigger signal based on a signal input from an external device;
a captured image generator unit configured to output a captured image by extracting one frame from the first video stream based on the trigger signal output from the trigger signal acquisition unit;
a frame interpolation unit configured to, with the captured image output from the captured image generator unit as an input, interpolate at least one frame image at the predetermined frame rate and output the captured image and the interpolated frame image over a period until a new captured image is input;
a storage controller unit configured to sequentially record the captured images output from the captured image generator unit as a second video stream in a storage and record the captured images and the interpolated frame images in array as a third video stream;
a reproduction controller unit configured to reproduce the second video stream or the third video stream recorded in the storage;
a timing signal acquisition unit configured to output multiple timing signals based on signals input from multiple types of external devices;
a labelling unit configured to assign explanation labels to the first video stream according to the timing signals; and
a live moving image storage controller unit configured to record, in the storage, the first video stream to which the explanation labels output from the labelling unit are assigned.

5. The recording and reproduction control device according to claim 4, wherein the reproduction controller unit is further configured to reproduce, at the predetermined frame rate, the frame images that are sampled at a period different from a period of the trigger signal from the third video stream.

6. The recording and reproduction control device according to claim 4, wherein the trigger signal is generated at a timing that is synchronized with a specific phase of an electrocardiogram based on information acquired from the electrocardiogram.

7. A recording and reproduction control method comprising:
outputting a first video stream by acquiring moving image data of a predetermined frame rate output from a camera;
outputting a trigger signal based on a signal input from an external device;
outputting a first captured image and a second captured image chronologically by extracting one frame from the first video stream based on the trigger signal;
with the first captured image and the second captured image as an input, interpolating at least one frame image at the predetermined frame rate and outputting the captured images and the interpolated frame images over a period until a new captured image is input;
sequentially recording the output captured images as a second video stream in a storage and recording the captured images and the interpolated frame images in array as a third video stream; and
reproducing the second video stream recorded in the storage, wherein
the frame image is a mixture image obtained by mixing the first captured image and the second captured image based on a time ratio of a time at which the first captured image was input and a time at which the second captured image was input.

8. The recording and reproduction control method according to claim 7, further comprising reproducing, at the predetermined frame rate, the frame images that are sampled at a period different from a period of the trigger signal from the third video stream.

9. The recording and reproduction control device according to claim 7, wherein the trigger signal is generated at a timing that is synchronized with a specific phase of an electrocardiogram based on information acquired from the electrocardiogram.

* * * * *